(12) United States Patent
Hajianpour (10) Patent No.: US 8,262,657 B2
(45) Date of Patent: Sep. 11, 2012

(54) EXTERNAL FIXATION APPARATUS WITH ADJUSTABLE PIN CLAMPING MEANS AND CONVERGENT BONE PINS

(75) Inventor: Mohammed Ali Hajianpour, Fort Lauderdale, FL (US)

(73) Assignee: Nutek Orthopaedics, Inc., Fort Lauderdale, FL (US)

( * ) Notice: Subject to any disclaimer, the term of this patent is extended or adjusted under 35 U.S.C. 154(b) by 667 days.

(21) Appl. No.: 12/316,830

(22) Filed: Dec. 17, 2008

(65) Prior Publication Data

US 2010/0082028 A1   Apr. 1, 2010

Related U.S. Application Data

(63) Continuation-in-part of application No. 11/893,582, filed on Aug. 16, 2007, now Pat. No. 7,717,916.

(51) Int. Cl.
*A61B 17/00* (2006.01)

(52) U.S. Cl. .......................................... 606/59; 606/280

(58) Field of Classification Search .................. 606/254, 606/257, 259, 280–299, 54–59, 53, 60
See application file for complete search history.

(56) References Cited

U.S. PATENT DOCUMENTS

| | | | |
|---|---|---|---|
| 4,554,915 A | | 11/1985 | Brumfield |
| 4,895,141 A | * | 1/1990 | Koeneman et al. .............. 606/54 |
| 5,000,166 A | * | 3/1991 | Karpf .............................. 606/250 |
| 5,127,914 A | * | 7/1992 | Calderale et al. ............... 606/65 |
| RE34,985 E | | 6/1995 | Pennig |
| 5,501,684 A | * | 3/1996 | Schlapfer et al. ............. 606/301 |
| 5,779,703 A | | 7/1998 | Benoist |
| 7,147,639 B2 | | 12/2006 | Berki et al. |
| 7,153,302 B1 | | 12/2006 | Hajianpour |
| 2003/0225407 A1 | * | 12/2003 | Estrada, Jr. ...................... 606/54 |
| 2005/0043730 A1 | * | 2/2005 | Janowski et al. ............... 606/56 |
| 2007/0055233 A1 | * | 3/2007 | Brinker ........................... 606/54 |
| 2007/0161994 A1 | * | 7/2007 | Lowery et al. .................. 606/61 |

FOREIGN PATENT DOCUMENTS

WO   WO 91/00111   8/1991

* cited by examiner

*Primary Examiner* — Eduardo C Robert
*Assistant Examiner* — Steven Cotroneo
(74) *Attorney, Agent, or Firm* — Ronald V. Davidge (57) ABSTRACT

An external fixation device for holding bone fragments in place includes a housing having a number of rotationally adjustable pin holders, each of which is held by a clamping member that simultaneously clamps the pin holder within an internal mounting surface of the housing and a bone pin within the pin holder. A first embodiment includes a number of internal mounting surfaces, each of which can include a single pin holder. A second embodiment includes one or two internal mounting surfaces, each of which holds a row of pin holders that is clamped in place by a single clamping member. Other embodiments include pin holders arranged so that bone pins, extending from a linearly extending or arcuate surface are concentrated in a region.

13 Claims, 10 Drawing Sheets

EXTERNAL FIXATION APPARATUS WITH ADJUSTABLE PIN CLAMPING MEANS AND CONVERGENT BONE PINS

CROSS-REFERENCE TO A RELATED APPLICATION

This is a continuation-in-part of a U.S. patent application Ser. No. 11/893,582, filed Aug. 16, 2007, now issued as U.S. Pat. No. 7,717,916 b2.

BACKGROUND OF THE INVENTION

1. Field of the Invention

This invention relates to apparatus for the external fixation of fractured bones, and, more particularly, to such apparatus having means for adjustably mounting and clamping a number of bone pins to a housing.

2. Summary of the Background Art

External fixation often provides the best method for holding bone fragments in place during the healing of a severe bone fracture, in which multiple bone fragments are formed. In the external fixation process, bone pins or wires ate surgically attached to the individual bone fragments and to intact sections of bone, so that a desired alignment of multiple fragments can be maintained during the healing process. The individual bone pins or wires are also attached to a frame that is external to the body to be held in a fixed configuration. Then, after the bone fragments have joined to one another in a satisfactory manner, the bone pins or wires are removed from the bones and from the body in another surgical procedure, With external fixation, an ability to hold individual bone fragments in place often makes in possible to achieve results that cannot be achieved using other conventional techniques, such as casting.

Since serious bone fractures can occur in many different ways in various parts of the body, forming various configuration of bone fragments, it is highly desirable that a device for external fixation should be configured in a variety of different ways, reducing the number of different types of fixation devices that need to be held in inventory to meet expected demands. To this end, the patent literature includes a number of descriptions of fixation devices that can be assembled from multiple elements in various ways or that can be adjusted to provide various configurational features.

One method to obtain this kind of flexibility has been to provide a plate having a number of holes defining locations in which bone pins or wires may be clamped, with only a variable subset of the holes being used in the treatment of a typical fracture. For example, U.S. Pat. No. 7,153,303 describes a fixture including several holes for clamping members to hold bone pins disposed within an elongated portion and a number of holes in a rectangular pattern, which can accommodate a variety of pin configurations. Such an arrangement is used, for example, to fasten the elongated portion of the fixture to the shaft of the radius bone within the arm and to attach various fragments within a broken wrist to a pattern of pins clamped within the rectangular array. A configuration for applying external fixation to a fractured tibia is also described as including a frame an elongated lower section for fastening the frame to the shaft of the tibia using bone pins extending along a straight line and an arcuate section extending from each side of the upper end of the elongated lower section for clamping bone pins extending into bone fragments within the upper portion of the tibia. U.S. Pat. No. 5,779,703 describes a bone organizer having a number of holes through which wires are attached to bone fragments.

Another method for obtaining flexibility within an external fixation device is to provide a number of clamping elements holding one or more bone pins, with the clamping elements being attached to one another by devices providing for pivotal adjustment. For example, U.S. Pat. No. 5,624,440 describes a fixture including a number of clamping elements, each of which clamps a pair of bone pins extending parallel to one another and a rod to which the clamping elements are attached by means of a pair of pivoting clamps providing for rotational adjustment and clamping about two axes perpendicular to one another. U.S. Pat. No. RE34,985 describes a fixation device having a pair of elongated carriers, each of which supports a pair of bone screws that are movable along the carrier by rotating a spindle. The carriers are joined to one another by a connector including a rigid rod and a ball at each end. The balls are received by partly spherical sockets that can be fixed relative to the balls through screws. U.S. Pat. No. 4,554,915 describes an external fixation frame including a fixation block from which one or more arms extend, with a ball and socket joint connecting each arm to the block for universal movement thereabout. Setscrews are provided for tightening the ball and socket joints. International Pat. Appl. Pub. No. WO 91/111 describes a fixation device having a pair of clamping members, each of which includes a row of holes into which bone pins may be inserted and clamped, with the clamping members being connected by a tube, into which a rod extends from one of the clamping members, while a ball from the other connecting member extends into a partially spherical hole within the tube. Setscrews are provided for clamping the rod and ball in place within the tube.

What is needed is a bone fixation device having the flexibility of adjusting the angle at which individual bone pins extend from a housing or frame, preferably with such an adjustment being provided through a clamping device that simultaneously clamps both the linear extension of the bone pin, along its length, and its angle relative to the housing or frame.

SUMMARY OF THE INVENTION

In accordance with a first aspect of the invention, apparatus is provided for the external fixation of bone fragments, with the apparatus comprising a housing including an elongated portion, a plurality of bone pins, and a plurality of pin mounting structures, which hold the bone pins. The pin mounting structures are spaced apart, extending along the elongated portion through a first distance. The plurality of pin mounting structures are configured to hold the plurality of bone pins to converge within a region of convergence substantially shorter than the first distance and spaced apart from the elongated portion. Each of the pin mounting structures is rotationally adjustable within the elongated portion to vary a location of a pin within the region of convergence.

Preferably, each of the pin mounting structures includes a pin holder, a mounting hole formed within the housing, and a clamping member. The pin holder includes a pin mounting surface holding one of the bone pins, a spherically rounded outer surface, and at least one deformable portion. The mounting hole includes a spherically rounded inner surface engaging the spherically rounded outer surface of the pin holder, an aperture extending outward through the housing from the spherically rounded outer surface toward the region of convergence, and a threaded inner surface. The spherically rounded inner surface, the aperture, and the threaded inner surface are coaxial about a central axis. The clamping member includes a threaded outer surface engaging the threaded inner surface of the mounting hole and a rounded surface engaging the pin holder. Engagement between the threaded outer surface of the clamping member and the threaded inner surface of the mounting hole holds the pin holder in place between the rounded surface of the clamping member and the spherically rounded inner surface of the mounting hole, and additionally deflects the deformable portion(s) of the pin holder to hold the bone pin in place within the pin holder.

In one embodiment, the elongated portion of the housing extends linearly in a first direction with the pin mounting structures being disposed within a first distance in the first direction along the elongated portion of the housing. The area of convergence is significantly shorter in the first direction than the first distance. The mounting hole axes extend toward the area of convergence at a plurality of angles.

In another embodiment, the elongated portion of the housing extends along an arc formed about an arc axis, with the area of convergence being formed around the arc axis and with the mounting hole axes extending toward the arc axis. Preferably, the elongated portion of the housing extends in a semicircle around the arc axis, with the housing additionally including a linear portion extending, parallel to the arc axis, from one or both ends of the elongated portion. Such a linear portion includes an additional plurality of pin mounting structure, holding bone pins extending toward the arc axis.

DETAILED DESCRIPTION OF THE INVENTION

Figure 1:
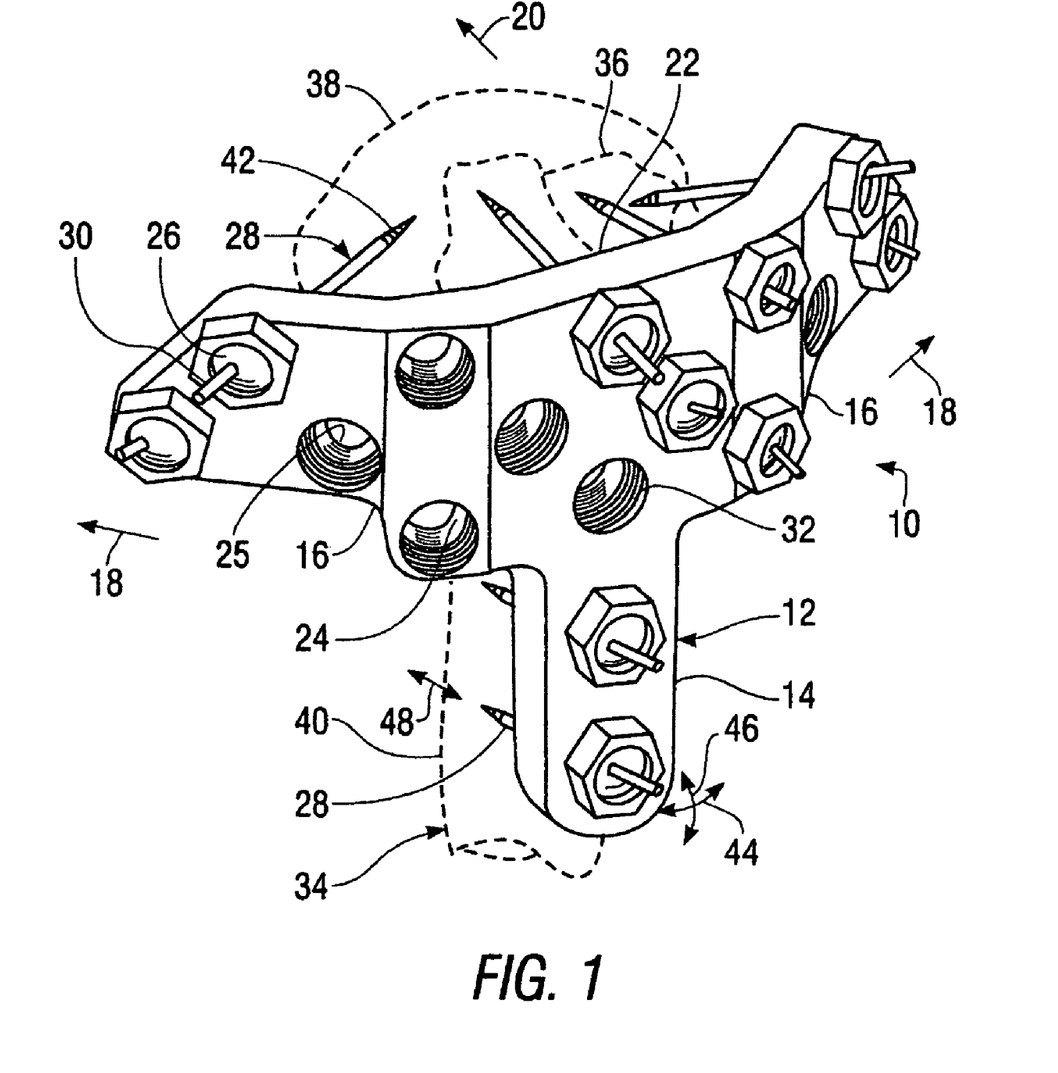
FIG. 1 is a perspective view of a device for external fixation of bone fragments, built in accordance with a first embodiment of the invention and shown as used for a proximal fracture of the humerus.

FIG. 1 is a perspective view of a device 10 for the external fixation of bone fragments, built in accordance with a first embodiment of the invention. The device 10 includes a housing 12 having a vertically elongated central portion 14 and a lateral portion 16 extending outward, in the directions of arrows 18, and rearward, in the direction of arrow 20, from each side of an upper end 22 of vertically elongated central portion 14: The vertically elongated central portion 14 includes a first plurality of the internal mounting surfaces 24; each of which extends outwardly from an aperture 25 within the housing 12, while each lateral portion 16 includes at least one of the internal mounting surfaces 24 extending from an aperture 25. Some of the internal mounting surfaces 24 mount pin holders 28 holding bone pins 28, with the pin holders 28 being held in place by clamping members 30 engaging threaded surfaces 32 of the housing 12. This arrangement provides for the placement of bone pins 28 at various levels extending downward from the upper end 22 of the vertically elongated central portion 14, with the lateral portions 16 being inclined relative to one another so that bone pins 28 can extend inward around a fracture area from these portions 16.

In the example of FIG. 1, the device 10 is shown with various bone pins 28 attached to a fractured humerus bone 34, holding a number of fragments 36 in place at an upper end 38 of the humerus bone 34, with bone pins 28 held within the vertically elongated central portion 14 of the housing 12 attached to the shaft portion 40 of the humerus bone 34. Each of the bone pins 28 includes a threaded end 42 that is driven into engagement with a portion of the bone 34 by a driving tool (not shown) rotating a non-circular surface (not shown) at an end of the bone pin 28 opposite the threaded end 42. After the bone pin 28 is fastened into place, the bone pin 28 is preferably cut off outwardly adjacent the pin holder 26 in which it is held to limit the distance through which the bone pin 28 extends outwardly from the device 10. The configuration of the device 10 is adjustable in several ways, with pin holders 26 being placed in a subset of the internal mounting surfaces 24, so that bone pins 28 are placed at locations appropriate for the external fixation of a particular fractured bone. In addition, the individual pin holders 26 are angularly adjustable so that each bone pin 28 can be adjusted and clamped in place through a vertical angle of adjustment 44 and through a horizontal angle of adjustment 46, with the bone pin 28 additionally being adjustable along its axis in the directions of arrows 48.

Figure 1A:
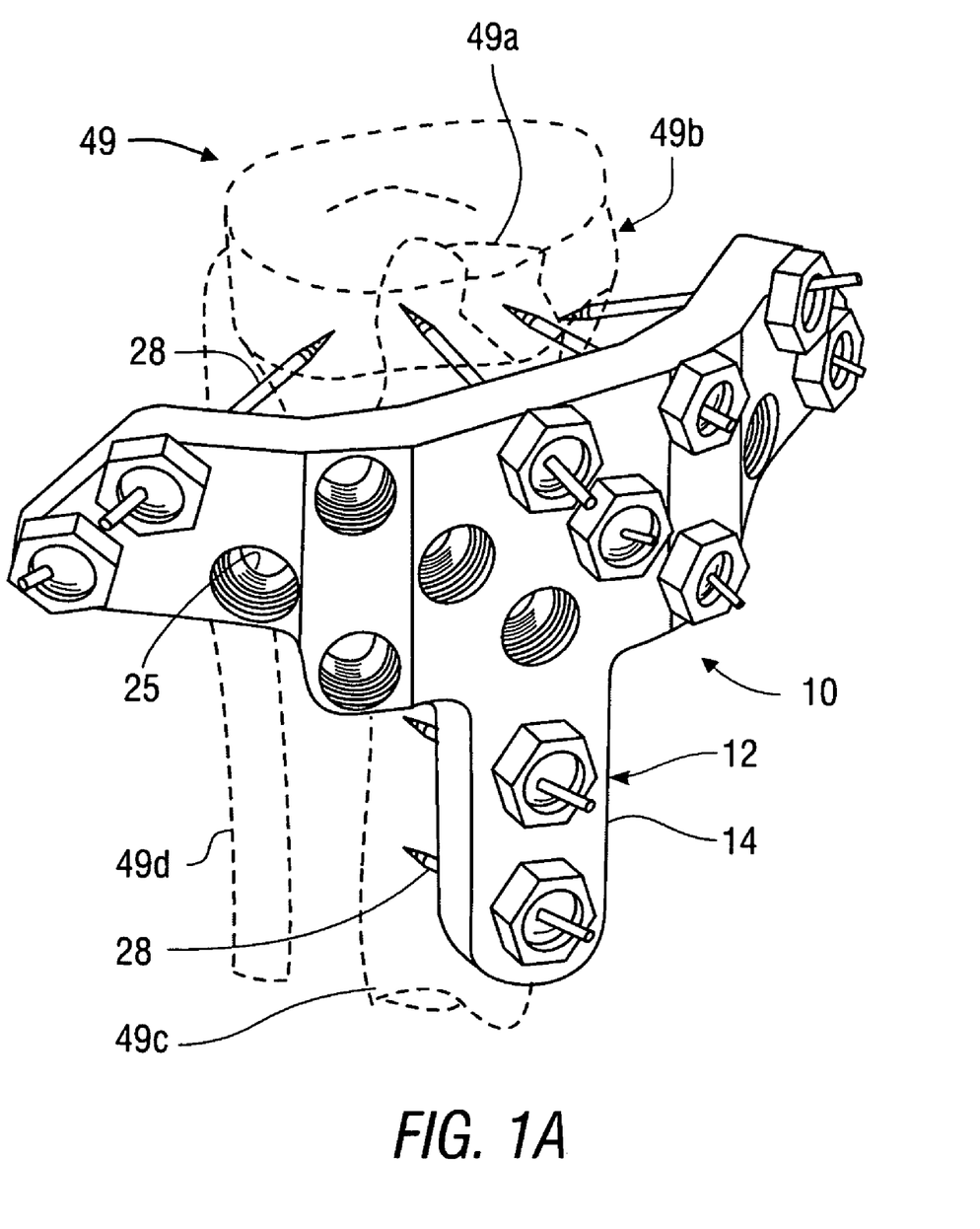
FIG. 1A is a perspective view of the device of FIG. 1, shown as used for a proximal fracture of the tibia.

FIG. 1A shows the device 10 with various bone pins 28 attached to a fractured tibia 49, holding a number of fragments 49a in place at the upper end 49b of the tibia, with bone pins 28 held within the vertically elongated portion 14 of the housing 12 attached to the shaft portion 49c of the tibia 49. To achieve non-bridging fixation, allowing movement of the leg and knee while maintaining the fixation of fragments 49a of the tibia 49, all bone pins 28 are fastened into the tibia 49 and fragments thereof 49a, with no bone pins being fastened into the fibia 49d or other bones.

Figure 2:
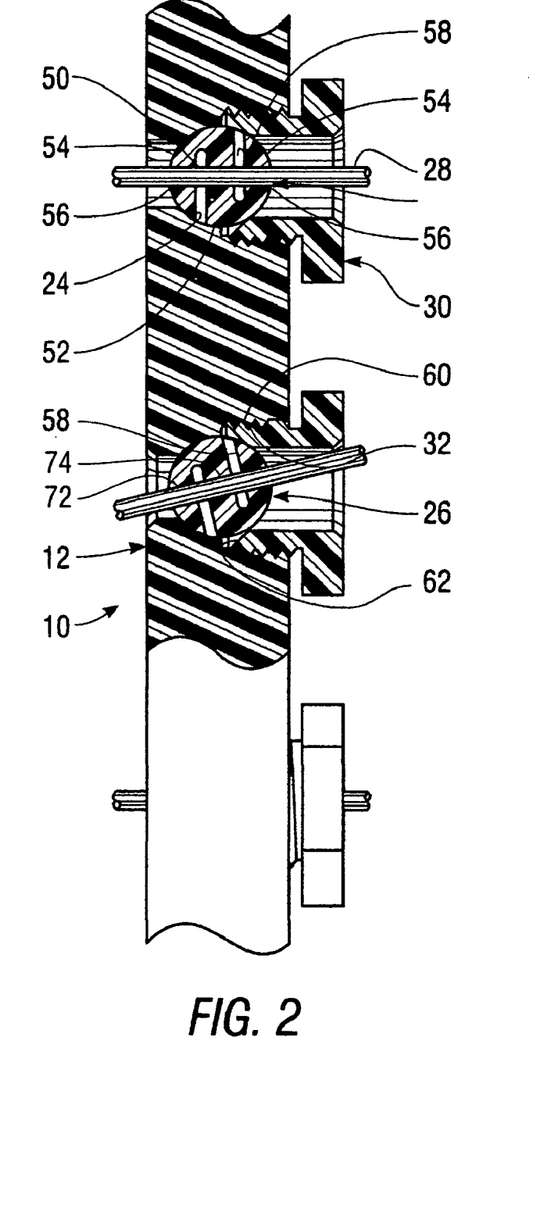
FIG. 2 is a fragmentary and partly cross-sectional lateral elevation of the device of FIG. 1.

FIG. 2 is a fragmentary and partly cross-sectional lateral elevation of the device 10, particularly showing features of the internal mounting surfaces 24 within the housing 12, of the pin holders 26, and of the clamping members 30. Each of the pin holders 26 includes a pin mounting hole 50, a spherically rounded surface 52 engaging an internal mounting surface 24 within the housing, and deformable portions 54 at each end 56 of the pin mounting hole 50. Each of the deformable portions 54 is formed by a slot 58 extending inward in a direction perpendicular to the pin mounting hole 50, extending across the pin mounting hole 50 and part of the way across the pin holder 26. Each of the of clamping members 30 clamps a pin holder 26 in place within the housing 12 and deflects the deformable portions 54 of the pin holder 26 to hold the pin 28 in place within the pin holder 26. Each clamping member 30 includes a threaded surface 60 and an annular surface 62 engaging a deformable portion 54 of a pin holder 26. The threaded surface 60 of each of the clamping members 30 engages one of the threaded surfaces 32 of the housing 12.

Thus, each of the bone pins 28 extends through an aperture 25 within the housing 12 at angles, in horizontal and vertical planes relative to the housing 12, that can be varied by rotation of the spherically rounded surface 52 of the pin holder 26 through which the bone pin 28 extends within the internal mounting surface 24. A bone pin may extend in a direction perpendicular to the aperture 25 or at an angle of inclination relative to such a direction of, for example, up to thirty degrees.

Figure 3:
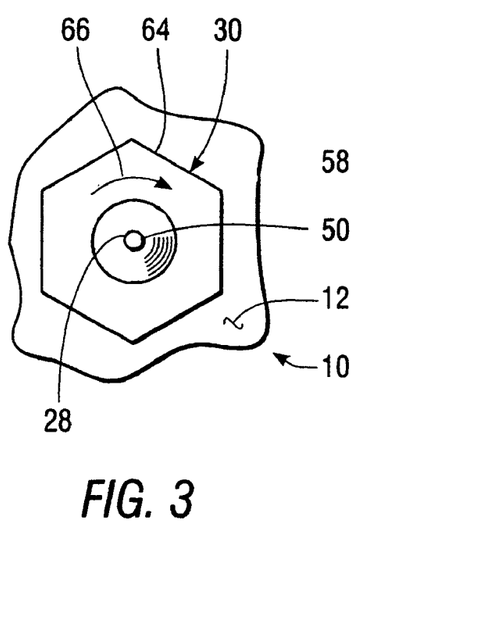
FIG. 3 is a fragmentary front elevation of the device of FIG. 1.

FIG. 3 is a fragmentary front elevation of the device 10, showing one of the clamping members 30, which is provided with a noncircular surface 64 to facilitate rotation of the clamping member 30. As the clamping member 30 is tightened by rotation in a first direction, indicated by arrow 66, an engagement force between the spherically rounded surface 52 of the pin holder 26 clamped in place within the housing 12 by the clamping member 30 and the internal mounting surface 24 within the housing 12 is increased to hold the pin holder 26 in place within the housing 12 and deflection of the deformable portions 54 of the pin holder is increased to hold the bone pin 28 in place within the pin holder 26. As each of the clamping members 30 is rotated opposite the first direction of arrow 66, the engagement force between the spherically rounded surface 52 of the pin holder 26 and the internal mounting surface 24 within the housing 12 is decreased to allow rotation of the spherically rounded surface 52 of the pin holder 26 within the internal mounting surface 24 of the housing 12 and to allow movement of the bone pin 28 within the pin mounting hole 50 of the pin holder 26. For example, the device 10 may be provided with a box wrench (not shown) for loosening and tightening the clamping members 30.

Figure 4:
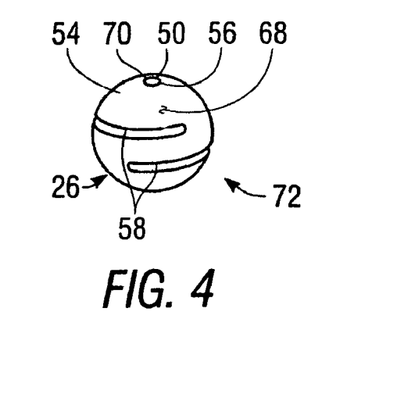
FIG. 4 is a perspective view of a pin holder within the device of FIG. 1.

FIG. 4 is a perspective view of one of one of the pin holders 26, which has a spherical external surface 68. The clamping member 30 includes a pair of slots 58 extending perpendicular to the pin mounting hole 50, inward across the pin mounting hole 50 and partly across the pin holder 26, so that a deformable portion 54 is formed between each end 56 of the pin mounting hole 50 and the slot 58 that is nearer to the end 56.

As shown in FIG. 3, the pin mounting hole 50 extends through a center of the spherical external surface 68, being divided by the slots 58 into a deflectable part 72 within each of the deformable portions 54 and a central part 74 extending between the slots 58. When the clamping member 30 is tightened by rotation in the direction of arrow 66 to increase an engagement force holding the pin holder 26 in place, the deformable portions 54 are deflected inward, bring the deflectable parts 72 of the pin mounting hole 50 out of alignment with the central part 74 thereof, so that the bone pin 28 is clamped in place within the pin mounting hole. Them, when the clamping member is loosened by rotation opposite the opposite the direction of arrow 66 to decrease the engagement force holding the pin holder 20 in place, the deformable portions 54 return outward, so that the deflectable parts 72 of the pin mounting hole 50 return into alignment with the central part 74 thereof, allowing movement of the bone pin 28 within the pin mounting hole 50. For example, the bone pin 28 may be rotated as much as thirty degrees from a central position in which the bone pin 28 extends perpendicularly from the housing 12.

Figure 5:
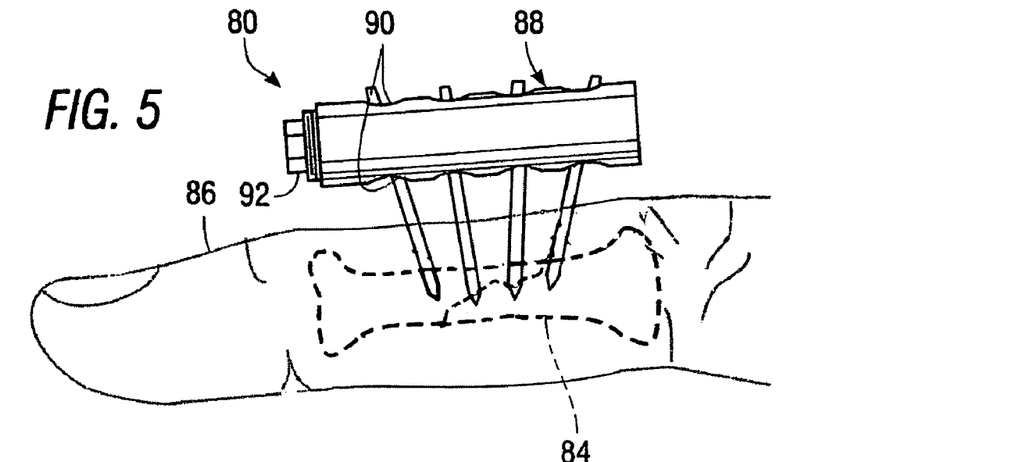
FIG. 5 is a side elevation of a device built in accordance with a first version of a second embodiment of the invention and shown attached to bone fragments within a finger.

FIG. 5 is a side elevation of a device 80 for external fixation of bone fragments, built in accordance with a second embodiment of the invention and shown with pins 82 attached to several fragments of bones 84 within a finger 86. The device 80 includes a housing 88, having a plurality of apertures 90 through which the pins 82 extend, and a first clamping member 92, which is turned to clamp the pins 82 in place within the housing 88.

Figure 6:
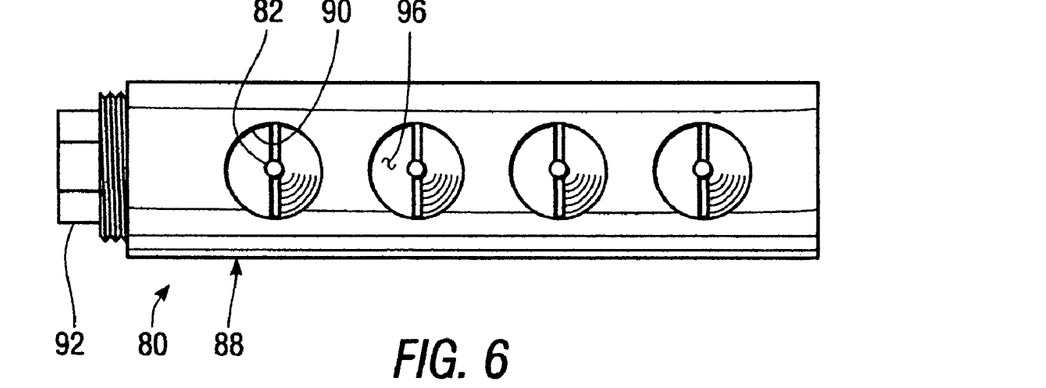
FIG. 6 is a plan view of the device of FIG. 5.
Figure 7:
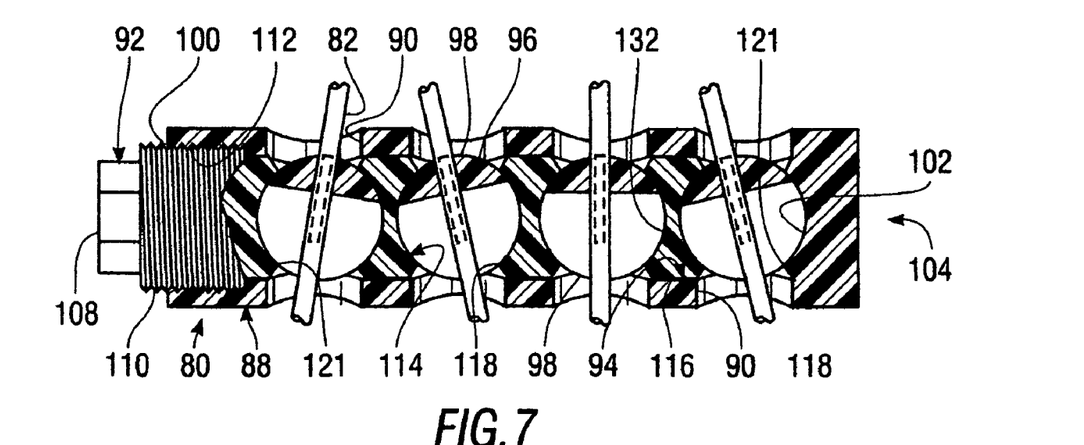
FIG. 7 is a cross-sectional side view of the device of FIG. 5.

Features of the device 80 will now be discussed with reference being made to FIGS. 6 and 7. FIG. 6 is a plan view of the device 80, while FIG. 7 is a cross-sectional side elevation thereof. The housing 88 includes a single internal mounting surface 94, with the single clamping member 92, clamping each of a plurality of pin holders 96 in place within the first internal mounting surface 94 and deflecting a deformable portion 98 of each of the pin holders 96 to hold the bone pin 82 therein in place. For example, the first internal mounting surface 94 is formed as an elongated cylinder having an open end 100 and a closed end 102, with the plurality of pin holders 96 disposed in a first row 104 within the first internal mounting surface 94. The first clamping member 92 is movable within the open end 100 of the elongated cylinder to provide a clamping force acting against the pin holder adjacent the open end 100 of the internal mounting surface 94. For example, the first clamping member is moved in the direction of arrow 106 by turning a non-circular portion 108 of the clamping member with a threaded portion 110 thereof in engagement with a threaded portion 112 of the housing 88. A clamping force, arising from the engagement between the clamping member 92 and the pin holder 96 adjacent the open end 100, is transmitted between the pin holders 96 adjacent one another within the first row 104. For example, the device 80 may be provided with a socket head wrench for loosening and tightening the clamping member 92.

Figure 8:
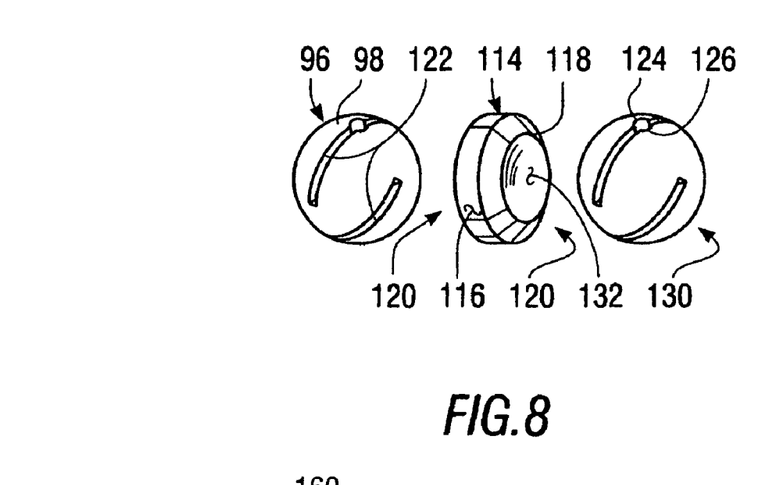
FIG. 8 is an exploded perspective views of adjacent pin holders and a spacer disposed therebetween within the device of FIG. 5

FIG. 8 is an exploded perspective view of two pin holders 96 and a spacer 114 disposed between the pin holders 96. Preferably, the device 80 additionally includes a spacer 114 between each pair of pin holders 96 adjacent one another in the first row 104, with the clamping force being transmitted between the pin holders 96 adjacent one another through the spacer 114. The spacer 114 includes a peripheral surface 116 engaging the first internal mounting surface 94 of the housing 88 between adjacent apertures 90 within the housing 88 and a circular edge 118 engaging the adjacent pin holder 96 at each side 120 of the spacer 114 to hold the pin holder 96 in place within the housing 88. Without the spacers 114, the pin holders 96 would be allowed to move into the adjacent apertures 90, so that the pin holders 96 would not be rigidly mounted within the first mounting surface 94. Preferably, as shown in FIG. 7, the first clamping member 92 and the closed end 102 of the first internal mounting surface 94 additionally also include a circular edge 121 engaging the adjacent pin holder 96 to hold the pin holder 96 in place within the housing 88.

Each of the pin holders 96 additionally includes a slot 122 extending inward from each end 124 of a pin mounting hole 126 to form a part of the deformable portion 98 of the pin holder 96 at each end 124 of the pin mounting hole 128. The slots 122 at each end 124 of the pin mounting hole 128 extend along the pin mounting hole 126, being disposed perpendicular to one another. Preferably, the slots 122 are formed to extend inward, across one another in a central portion 130 of the pin holder 96, so that the central portion 130 can be deflected by contact with a concave surface 132 of the spacer 114, even if one of the slots 122 is positioned to extend between the concave surfaces 132 of spacers 114 at either side of the pin holder 96.

Thus, each of the bone pins 82 extends through an aperture 90 within the housing 88 at angles, in directions perpendicular to one another, that can be varied by rotation of the spherically rounded pin holder 96 through which the bone pin 28 extends within the internal mounting surface 94. A bone pin may extend in a direction perpendicular to the aperture 90 or at an angle of inclination relative to such a direction of, for example, up to thirty degrees.

Figure 9:
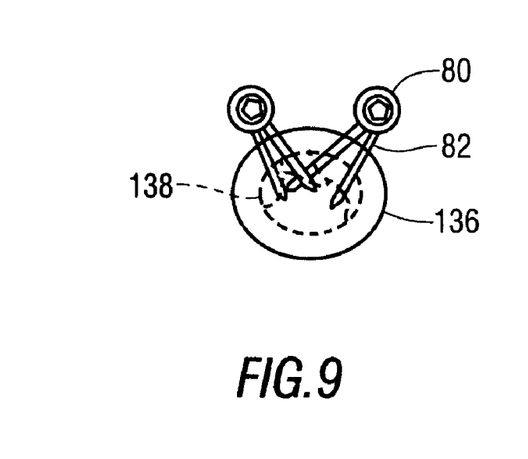
FIG. 9 is a partly sectional end view of a finger having two of the devices of FIG. 5 attached to bone fragments.

FIG. 9 is a partly sectional end view of a finger 136 with two of the devices 80 holding bone pins 82 in engagement with bone fragments 138. Two or more of the devices 80 may be used in this way so that the bone pins 82 can be directed from various locations extending around the bone fragments.

While the pin holders 96, 134 have been described in terms of use with the device 90 of FIGS. 5-7, it is understood that such pin holders 96, 134 can alternately be used with a device otherwise as described above in reference to FIGS. 1-3, with deformable portions 98, 150 being deflected in response to tightening the clamping member 30 to hold pins in place within the pin holders 56, 134.

Figure 10:
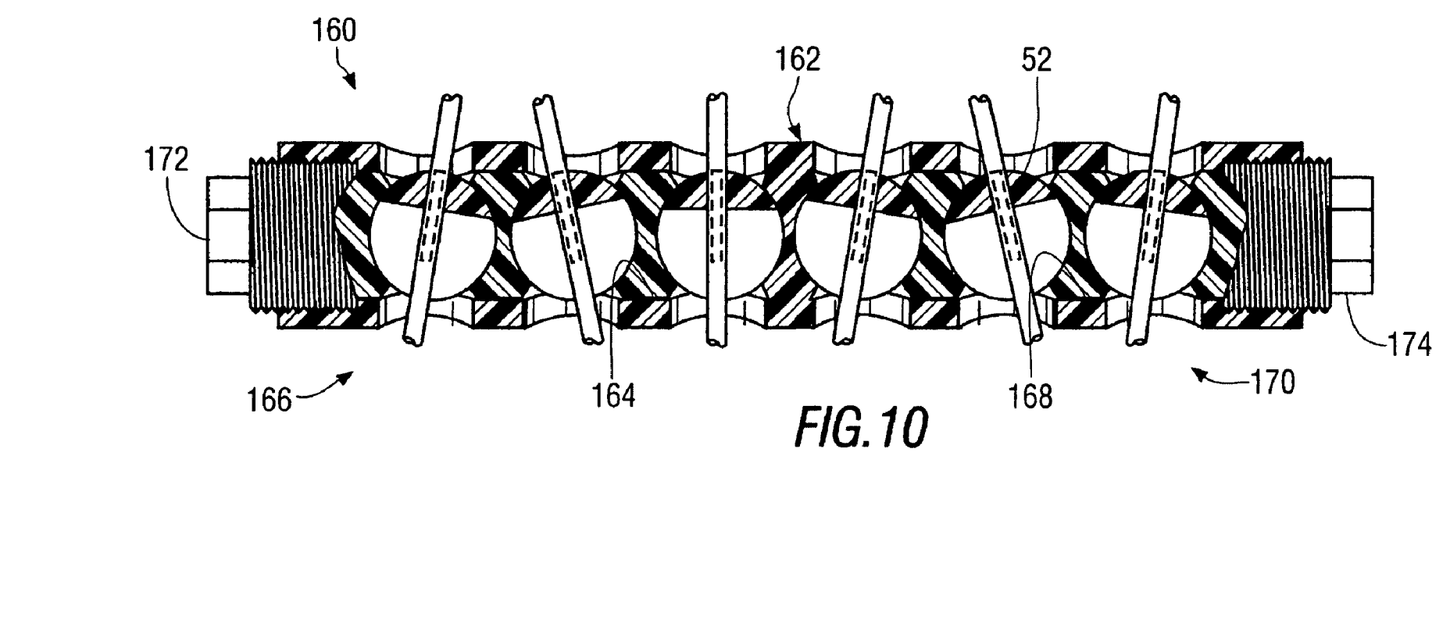
FIG. 10 is a cross-sectional side view of a device built in accordance with a second version of the second embodiment of the invention.

FIG. 10 is a cross-sectional side elevation of a device 160 built in accordance with a second version of the second embodiment of the invention to include a housing 162 having both a first internal mounting surface 164 holding a plurality of pin holders 52 in a first row 166 and a second internal mounting surface 168 holding a plurality of pin holders 52 in a second row 170. The device 160 additionally includes a first clamping device 172, which is turned to clamp and release all of the pin holders 52 in the first row 166, and a second clamping device 174, which is used to clamp and release all of the pin holders 52 in the second row 170. Other features of the device 100 are as described above in reference to FIGS. 5-9 for the device 80 built in accordance with the first version of the second embodiment of the invention. While the example of FIG. 10 shows three pin holders 52 held within each of the internal mounting surfaces 168, it is understood that each of the internal mounting surfaces in general can be configured to hold two or more pin holders 52.

Figure 11:
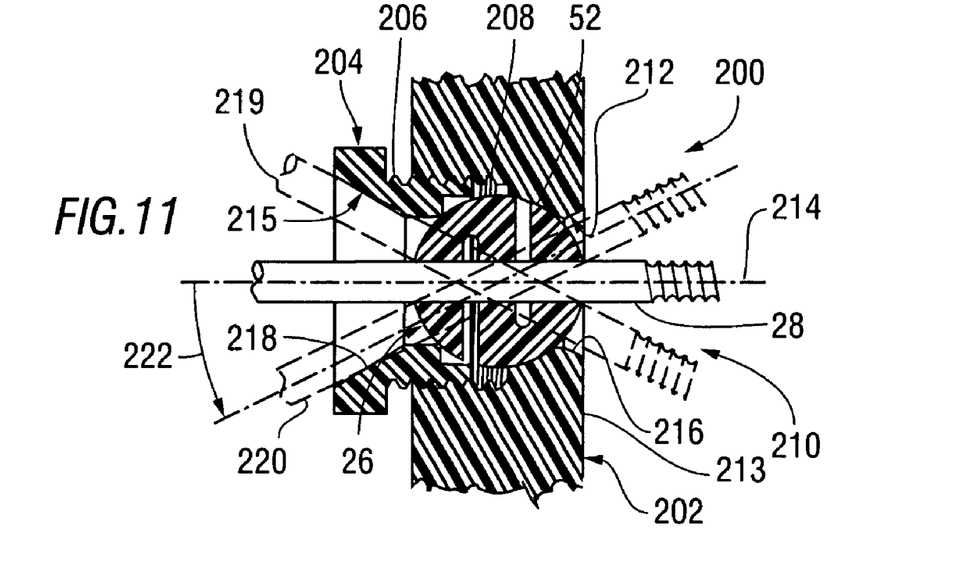
FIG. 11 is a transverse cross-sectional elevation of a pin mounting structure within a housing built in accordance with a third embodiment of the invention.

While a small example of the device 80 has been shown in FIG. 5, being applied for the fixation of bones within a finger, it is understood that the device 80 and the device 160 of FIG. 2 may be built in any size, having any number of pin holders 96, for the fixation of bone fragments in any long bones, including the tibia and the humerus FIG. 11 is a transverse cross-sectional elevation of a pin mounting structure 200 within a housing 202 built in accordance with a third embodiment of the invention. Parts similar to those of the first embodiment, as described above in reference to FIGS. 1-4, are accorded reference numbers similar to those used in the description of the first embodiment. A pin 28 is held within a pin holder 26, which is configured as described above in reference to FIG. 3, and which is clamped in place by a clamping member 204 having an outer threaded surface 206 engaging an inner threaded surface 208 within a mounting hole 210 of the housing 202. The mounting hole 210 includes a spherically rounded inner surface 211, engaging a spherical surface 52 of the pin holder 28, and an aperture 212, extending to a surface 213 of the housing 202. Within the mounting hole 210, the inner threaded surface 208, the spherically rounded inner surface 211, and the aperture 212 are coaxial with one another about a central axis 214. The aperture 212 and a clearance hole 215, extending through the clamping member 204, include truncated conical surfaces 216, 218. These truncated conical surfaces 216, 218 together allow movement of the pin 28 between the position indicated by dashed lines 219 and the position indicated by dashed lines 220. For example, the pin 28 may be moved through an angle 222 of thirty degrees from the central axis 214 of the mounting hole 210 and at any angle 226 around the central axis 214.

Figure 12:
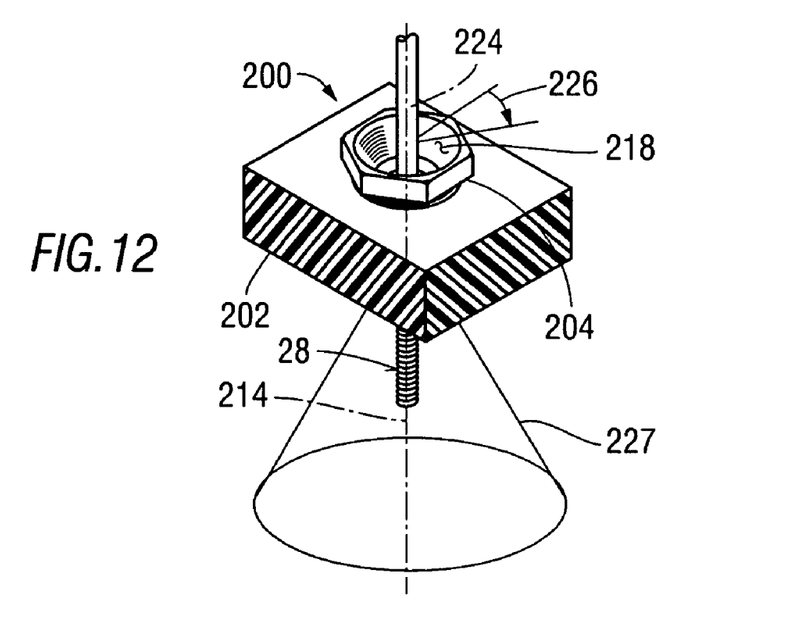
FIG. 12 is a perspective view of the pin mounting structure of FIG. 11.

FIG. 12 is a perspective view of the pin mounting structure 200, showing the bone pin 28 as being adjustable within a conical region 227 about the central axis 224.

Figure 13:
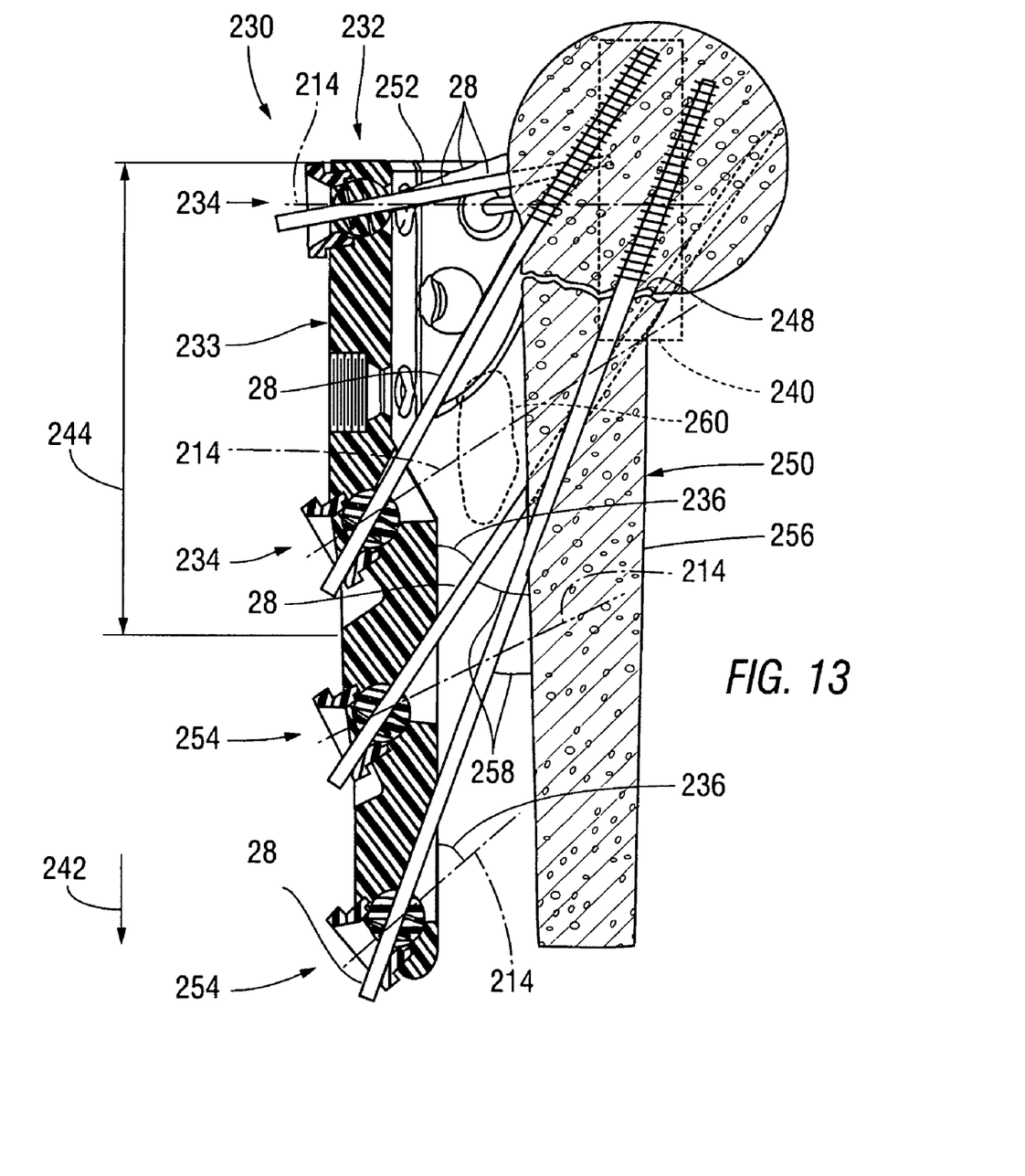
FIG. 13 is a lateral cross-sectional view of a bone fixation device built in accordance with the third embodiment, including a number of the pin mounting structures of FIG. 11.

FIG. 13 is a lateral cross-sectional view of a bone fixation device 230 built in accordance with the third embodiment of the invention to include a housing 232 having an elongated portion 233 with a number of pin mounting structures 234, each configured as described above in reference to FIG. 12, except that the central axes 214 of the mounting holes 231 are disposed at various angles 236 relative to a surface 238 of the housing 232. The pin mounting structures 234 are additionally arranged so that the central axes 214 converge within a region of convergence 240 that is spaced apart from the elongated portion 233. In addition, as described above in reference to FIG. 12, the bone pins 28 may be individually adjusted within conical regions 227 about the central axes 214, allowing further movement of the pins 28 within the region of convergence 240. This arrangement provides for placing a number of pins within the region of convergence 240, with the pins 28 entering the region from a wide variety of angles. For example, the region of convergence 240 may be located in a region of one or more fractures occurring within a bone, with the pins 28 being variously employed to hold bone fragments in place during the healing process. The housing 232 extends in a first direction of arrow 242, with the pin mounting structures 234 being disposed within a first distance 244. The region of convergence 240 is substantially shorter, in the first direction of arrow 242, than the first distance 244, allowing a concentration of the bone pins 28 within the region of convergence 240 to be much greater than the concentration of the bone pins along the surface 238 of the elongated portion 233.

In the example of FIG. 13, the bone fixation device 230 is shown providing fixation for a proximal fracture 248 of the humerus 250, with surrounding tissues not being shown for clarity. In addition to the pin mounting structures 234, the bone fixation device 230 includes various features, such as outward extending sections 252 of the housing 232 supporting additional bone pins 28, and such as a pin mounting structure 254 that is outside the first distance 244. Due to the adjustability provided within the pin mounting structure 254 a pin 28 held by this structure 254 extends into the region of convergence 240 after entering the shaft portion 256 of the humerus 250 at a low angle 258. Using the flexibility of bone pin placement provided within the bone fixation device 230, regions 260 within the tissue adjacent to the fracture 248 having concentrations of nerves, ligaments, blood vessels, etc. that cannot be disturbed without significant damage to the patient can readily be avoided in the placement of bone pins 28. Since all of the bone pins 28 are fastened into the humerus 250, the fixation device 230 does not bridge the shoulder joint, allowing movement while holding various bone fragments in place.

Figure 14:
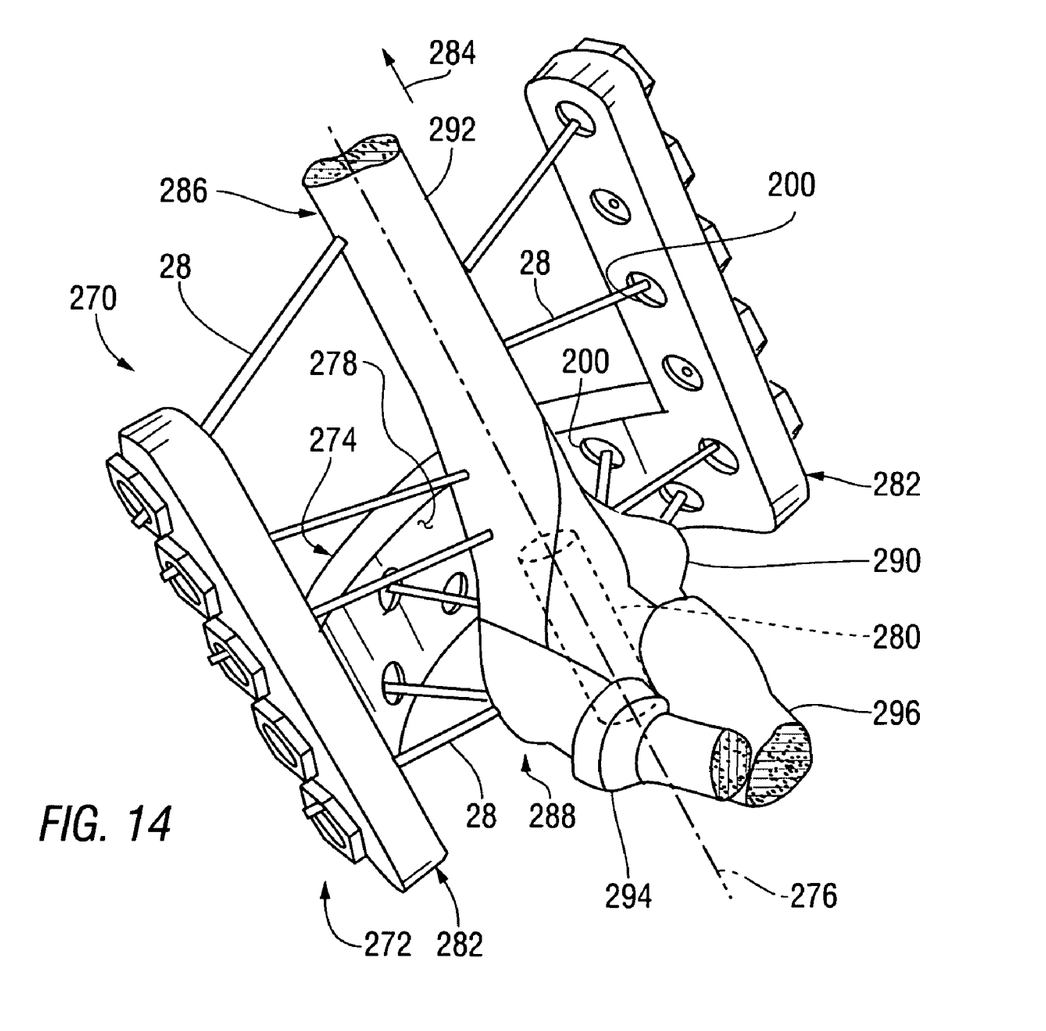
FIG. 14 is a perspective view of a fixation device built in accordance with a fourth embodiment of the invention, shown as used with a distal fracture of the humerus.

FIG. 14 is a perspective view of a fixation device 270 built in accordance with a fourth embodiment of the invention with a housing 272 including an arcuate elongated portion 274 formed as an arc having an arc axis 276. A plurality of bone pins 28 extend from an arcuate surface 278, also formed about the arc axis 276, Each of the bone pins 28 is adjustably held in place by a pin mounting structure 200, configured as described above in reference to FIG. 12. The central axis 214 of each of the pin mounting structures 200 passes through the arc axis 276, so that the central axes 214 are seen to converge upon a region of convergence 280 extending around the arc axis 276. In addition, the housing 270 includes a linearly elongated portion 282 extending from each end of the arcuate elongated structure 274. The linearly elongated portions 282 extend in the same direction, indicated by arrow 284, parallel to the arc axis 276. Each of the linearly elongated portions 282 includes another plurality of bone pins 28, extending toward the arc axis 276, with each of the bone pins 28 being adjustably held in place by a pin mounting structure 200.

In the example of FIG. 14, the fixation device 270 is shown as used to treat a fractured distal humerus 286, with the arcuate elongated portion 274 extending partly around the fractured area 288 at the distal end of the humerus 286 to hold various bone fragments 290 in place, and with the linearly elongated portions 282 extending along the bone shaft 292 to hold the fixation device 270 itself in place using bone pins 28 extending into the bone shaft 292. Since none of the bone pins 28 extend into the radius 294 or the ulna 296, the fixation device does not bridge across the elbow joint, allowing movement at the joint while holding the fragments together.

Figure 15:
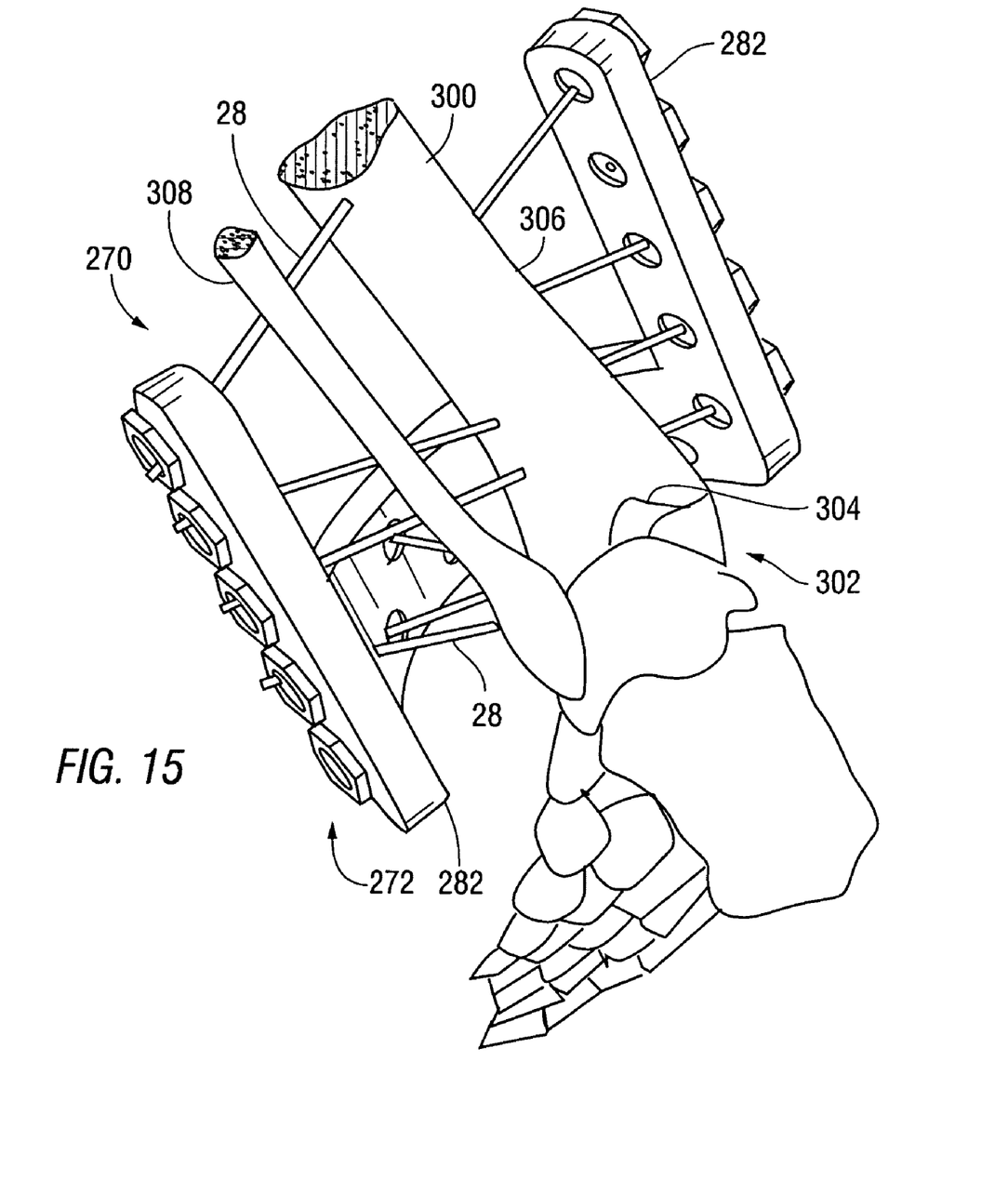
FIG. 15 is a perspective view of the fixation device of FIG. 14, shown as used with a distal fracture of the tibia.

FIG. 15 is a perspective view of the fixation device 270 as used to provide fixation for a fractured distal tibia 300, with the arcuate elongated portion 274 extending partly around the fractured area 302 to hold various bone fragments 304 in place, and with the linearly elongated portions 282 extending along the bone shaft 306 to hold the fixation device 270 in place using bone pins 28 extending into the bone shaft 306. Since none of the bone pins 28 extend into the fibia 308 or other bones, except for the tibia 300, non-bridging fixation is achieved.

Figures 16, 17:
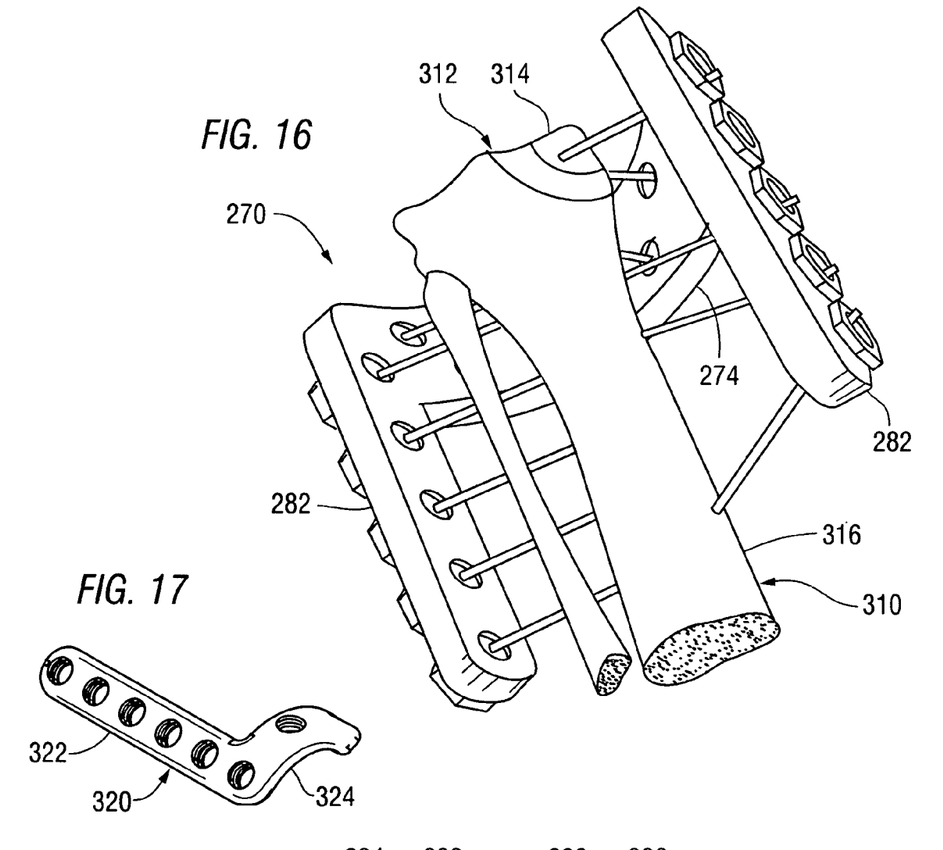
FIG. 16 is a perspective view of the fixation device of FIG. 14, shown as used with a proximal fracture of the tibia.
FIG. 17 is a perspective view of an alternative fixation device housing additionally built in accordance with the fourth embodiment.

FIG. 16 is a perspective view of the fixation device 270 as used to provide fixation for a fractured proximal tibia 310, as shown in a dorsal view, with the arcuate elongated portion 274 extending partly around the fractured area 312 to hold various bone fragments 314 in place, and with the linearly elongated portions 282 extending along the bone shaft 316 to hold the fixation device 270 in place using bone pins 28 extending into the bone shaft 316. Again, since none of the bone pins 28 extend into the fibia 318 or other bones, except for the tibia 310, non-bridging fixation is achieved.

FIG. 17 is a perspective view of a housing 320 for a fixation device, additionally built in accordance with the fourth embodiment of the invention, with only a single linearly elongated portion 322, extending from one of the ends of an arcuate elongated portion 324. Such fixation devices may be built in various sizes, with larger devices being used for attachment to bones of the arms and legs, and with smaller devices being used to provide fixation for fractured phalanges. Both the overall size of the fixation device and the size of the mounting devices 200 (shown in FIGS. 12 and 13) may be reduced to provide a greater density of smaller pins for use with a fractured phalange. In addition, the housings 272, 320 are preferably composed of a thermoplastic resin that can be easily cut if it is necessary to shorten a part of the housing.

Figure 18:
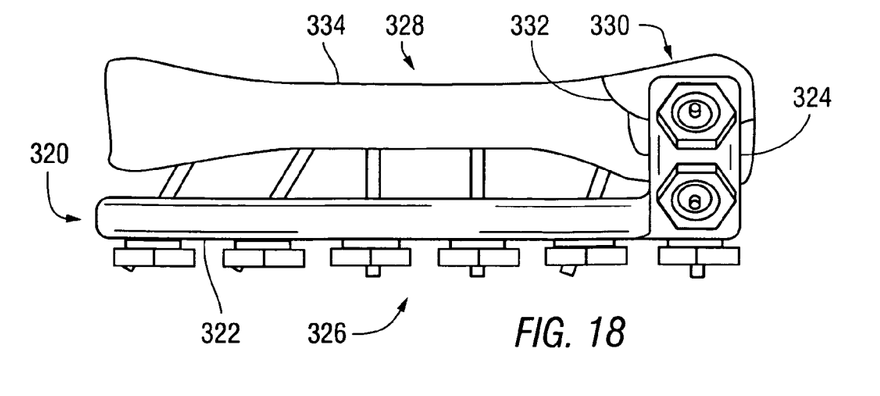
FIG. 18 is an elevation of a fixation device using the housing of FIG. 17, shown as used with a fractured phalange.

FIG. 18 is a perspective view of a fixation device 326, including the housing 320, as used to provide fixation for a fractured phalange 328, with the arcuate elongated portion 324 extending partly around the fractured area 330 to hold various bone fragments 332 in place, and with the linearly elongated portion 322 extending along a bone shaft 334 to hold the fixation device 326 in place using bone pins 28 extending into the bone shaft 334. Again, since all of the bone pins 28 extend through the phalange 328 and fragments thereof, non-bridging fixation is achieved.

While the invention has been described in terms of its preferred embodiments with some degree of particularity, it is understood that this description has been given only by way of example, and that many variations can be made without departing from the spirit and scope of the invention, as defined in the appended claims.

What is claimed is:

1. Apparatus for external fixation of bone fragments, comprising an integral housing including an elongated portion having outward-facing and inward-facing surfaces, at least three bone pins, and at least three pin mounting structures, spaced apart along a line extending along the elongated portion of the housing through a first distance, wherein the elongated portion of the housing and the mounting holes forming portions of the at least three pin mounting structures extend along an arcuate line formed about an arc axis, wherein the housing additionally includes a first linear portion extending from a first end of the arc axis, wherein the first linear portion includes at least three additional pin mounting structures, spaced apart along a straight line parallel to the arc axis, holding bone pins extending toward the arc axis, and wherein each of the pin mounting structures comprises a pin holder including a spherically rounded outer surface, a pin mounting surface holding one of the bone pins and at least one deformable portion, a mounting hole formed within the housing, including a spherically rounded inner surface engaging the spherically rounded outer surface of the pin holder and an aperture extending outward through the housing between the spherically rounded outer surface and the inward-facing surface of the housing, a threaded inner surface, coaxial with the spherically rounded inner surface and the aperture about the central axis, wherein the central axis of each of the mounting holes is disposed perpendicular to the arcuate line to extend to the arc axis at an angle different from an angle at which the central axis of each other mounting hole is disposed, so that the bone pins are held to converge within a region of convergence, formed around the arc axis to be substantially shorter than the first distance and spaced apart from the elongated portion, and wherein each of the pin holders is rotationally adjustable within the elongated portion to vary a location of a pin within the region of convergence, a clamping member having a threaded outer surface and a rounded surface engaging the pin holder, wherein engagement between the threaded outer surface of the clamping member and the threaded inner surface of the mounting hole holds the pin holder in place between the rounded surface of the clamping member and the spherically rounded inner surface of the mounting hole, and additionally deflects the at least one deformable portion of the pin holder to hold the bone pin in place within the pin holder.

2. The apparatus of claim 1, wherein the housing additionally includes a second linear portion extending from a second end of the elongated portion in a first direction, parallel to the arc axis, and the second linear portion includes at least three additional pin mounting structures, spaced apart along a straight line parallel to the arc axis holding bone pins extending toward the arc axis.

3. Apparatus for external fixation of bone fragments, comprising an integral housing including an elongated portion having a flat surface, a plurality of bone pins; and at least three pin mounting structures holding the bone pins to extend outward from the flat surface, wherein:

the pin mounting structures are spaced apart, extending along a straight line within the elongated portion, each of the pin mounting structures comprises a pin holder, including a pin mounting surface holding one of the bone pins and a spherically rounded outer surface; a clamping member having a threaded outer surface and a rounded surface engaging the pin holder, a mounting hole formed within the housing, including a spherically rounded inner surface engaging the spherically rounded outer surface of the pin holder, a threaded inner surface, coaxial with the spherically rounded inner surface and the aperture about the central axis, engaging the threaded outer surface of the pin mounting structure, and an aperture extending outward through the housing from the spherically rounded outer surface to the flat surface, the spherically rounded inner surface and the aperture are coaxial about a central axis, and wherein the pin mounting structures are arranged so that central axes of the mounting holes are arranged at a plurality of angles relative to the flat surface so that the bone pins are held to converge within a region of convergence substantially shorter than the first distance and spaced apart from the elongated portion, each of the pin holders is rotationally adjustable within the elongated portion to vary a location of a pin within the region of convergence, the pin mounting surface within each of the pin holders is formed as a hole extending in a straight line through a center of the spherically rounded surface of the pin mounting structure between first and second ends of the pin mounting structure, each of the pin holders additionally comprises a first slot, perpendicular to the pin mounting surface, extending across the pin mounting structure and partially across the pin holder, displaced inward from the first end of the pin mounting structure, a central part extending adjacent the first slot past a center of the spherically rounded outer surface of the holder, and a first deflectable portion extending between the first slot and the first end of the pin mounting structure, as each of the clamping members is rotated in a first rotational direction in contact with one of the pin holders, an engagement force between the spherically rounded surface of the pin holder and the internal mounting surface within the housing is increased to hold the pin holder in place within the housing, and deflection of the first deflectable portion of the pin holder is increased, moving a portion of the pin mounting hole within the first deflectable portion out of alignment with a portion of the pin mounting hole extending through the central part of the pin holder to hold the bone pin in place within the pin holder, and as each of the clamping member is rotated opposite the first rotational direction in contact with one of the pin holders, the engagement force between the spherically rounded surface of the pin holder and the internal mounting surface within the housing is decreased to allow rotation of the spherically rounded surface of the pin holder within the internal surface of the housing and wherein the deflection of the first deflectable portion of the pin holder is decreased, returning the portion of the pin mounting hole within the first deflectable portion into alignment with the portion of the pin mounting hole extending through the central part of the pin holder to allow movement of the bone pin within the pin holder.

4. The apparatus of claim 3, wherein each of the pin holders additionally includes a second slot, perpendicular to the pin mounting surface, extending across the pin mounting structure and partially across the pin holder, displaced inward from the second end of the pin mounting structure the central part of each pin holder extends between the first and second slots of the pin holder, each of the pin holders additionally includes a second deformable portion extending between the second slot and the second end of the pin mounting structure, as each of the clamping members is rotated in the first rotational direction in contact with one of the pin holders, deflection of the second deflectable portion of the pin holder is increased, moving a portion of the pin mounting hole within the second deflectable portion out of alignment with a portion of the pin mounting hole extending through the central part of the pin holder to hold the bone pin in place within the pin holder, and as each of the clamping members is rotated opposite the first rotational direction in contact with one of the pin holders, the deflection of the second deflectable portion of the pin holder is decreased, returning the portion of the pin mounting hole within the second deflectable portion into alignment with the portion of the pin mounting hole extending through the central part of the pin holder to allow movement of the bone pin within the pin holder.

5. Apparatus for external fixation of bone fragments, comprising an integral housing including an arcuate portion having an arcuate surface formed as an arcuate cylinder about an arc axis, a plurality of bone pins; and at least three pin mounting structures holding the bone pins to extend inward from the arcuate surface, wherein the pin mounting structures are spaced apart, extending along an arcuate line on the elongated portion, a clamping member having a threaded outer surface and a rounded surface engaging the pin holder, each of the pin mounting structures additionally comprises a pin holder including a pin mounting surface holding one of the bone pins, a spherically rounded outer surface; a mounting hole formed within the housing, including a spherically rounded inner surface engaging the spherically rounded outer surface of the pin holder and an aperture extending outward through the housing from the spherically rounded outer surface to the flat surface, and the spherically rounded inner surface and the aperture are coaxial about a central axis, and wherein the pin mounting structures are arranged so that central axes of the mounting holes are arranged to extend through the arc axis, each of the mounting holes additionally includes a threaded inner surface, coaxial with the spherically rounded inner surface and the aperture about the central axis, engaging the threaded outer surface of the pin mounting structure, the pin mounting surface within each of the pin holders is formed as a hole extending in a straight line through a center of the spherically rounded surface of the pin mounting structure between first and second ends of the pin mounting structure, each of the pin holders additionally comprises a first slot, perpendicular to the pin mounting surface, extending across the pin mounting structure and partially across the pin holder, displaced inward from the first end of the pin mounting structure, a central part extending adjacent the first slot past a center of the spherically rounded outer surface of the holder, first deflectable portion extending between the first slot and the first end of the pin mounting structure, as each of the clamping members is rotated in a first rotational direction in contact with one of the pin holders, an engagement force between the spherically rounded surface of the pin holder and the internal mounting surface within the housing is increased to hold the pin holder in place within the housing, and deflection of the first deflectable portion of the pin holder is increased, moving a portion of the pin mounting hole within the first deflectable portion out of alignment with a portion of the pin mounting hole extending through the central part of the pin holder to hold the bone pin in place within the pin holder, and as each of the clamping members is rotated opposite the first rotational direction in contact with one of the pin holders, the engagement force between the spherically rounded surface of the pin holder and the internal mounting surface within the housing is decreased to allow rotation of the spherically rounded surface of the pin holder within the internal surface of the housing and wherein the deflection of the first deflectable portion of the pin holder is decreased, returning the portion of the pin mounting hole within the first deflectable portion into alignment with the portion of the pin mounting hole extending through the central part of the pin holder to allow movement of the bone pin within the pin holder.

6. The apparatus of claim 5, wherein:

the housing additionally comprises a first linearly elongated portion having an inner surface extending in a first direction, parallel to the arc axis, from a first end of the arcuate portion, a first additional plurality of bone pins, and at least three additional pin mounting structures, spaced apart along a straight line parallel to the arc axis to hold the bone pins to extend inward, toward the arc axis, each of the pin mounting structures in the first linearly elongated portion comprises a pin holder including a pin mounting surface holding one of the bone pins, a spherically rounded outer surface, and at least one deformable portion;

each of the pin mounting structures in the first linearly elongated portion additionally comprises a mounting hole formed within the housing, including a spherically rounded inner surface engaging the spherically rounded outer surface of the pin holder, an aperture extending outward through the housing from the spherically rounded outer surface to the flat surface, and a threaded inner surface, engaging the threaded outer surface of the pin mounting structure, each of the pin mounting structures in the first linearly elongated portion additionally comprises a clamping member having a threaded outer surface engaging the threaded inner surface of the mounting hole and a rounded surface engaging the pin holder, in each of the pin mounting structures within the first linearly elongated portion, the spherically rounded inner surface, the aperture, and the threaded inner surface of the mounting hole are coaxial about a central axis, with central axes of the mounting holes arranged to extend to the arc axis, and engagement between the threaded outer surface of the clamping member and the threaded inner surface of the mounting hole holds the pin holder in place between the rounded surface of the clamping member and the spherically rounded inner surface of the mounting hole, and additionally deflects the at least one deformable portion of the pin holder to hold the bone pin in place within the pin holder.

7. The apparatus of claim 6, wherein:

the housing additionally comprises a second linearly elongated portion having an inner surface extending in the first direction, parallel to the arc axis, from a second end of the arcuate portion, a second additional plurality of bone pins, and at least three additional pin mounting structures to hold the bone pins to extend inward, toward the arc axis, each of the pin mounting structures in the second linearly elongated portion comprises a pin holder including a pin mounting surface holding one of the bone pins, a spherically rounded outer surface, and at least one deformable portion;

each of the pin mounting structures in the second linearly elongated portion additionally comprises a mounting hole formed within the housing, including a spherically rounded inner surface engaging the spherically rounded outer surface of the pin holder, an aperture extending outward through the housing from the spherically rounded outer surface to the flat surface, and a threaded inner surface, engaging the threaded outer surface of the pin mounting structure, each of the pin mounting structures in the second linearly elongated portion additionally comprises a clamping member having a threaded outer surface engaging the threaded inner surface of the mounting hole and a rounded surface engaging the pin holder, in each of the pin mounting structures within the second linearly elongated portion, the spherically rounded inner surface, the aperture, and the threaded inner surface of the mounting hole are coaxial about a central axis, the pin mounting structures are arranged so that central axes of the mounting holes are arranged to extend toward the arc axis, and engagement between the threaded outer surface of the clamping member and the threaded inner surface of the mounting hole holds the pin holder in place between the rounded surface of the clamping member and the spherically rounded inner surface of the mounting hole, and additionally deflects the at least one deformable portion of the pin holder to hold the bone pin in place within the pin holder.

8. Apparatus for external fixation of bone fragments, comprising an integral housing including an elongated portion having outward-facing and inward-facing surfaces, at least three bone pins, and at least three pin mounting structures, spaced apart along a line extending along the elongated through a first distance, wherein each of the pin mounting structures comprises a pin holder including a spherically rounded outer surface, a pin mounting surface holding one of the bone pins and at least one deformable portion, wherein the pin mounting surface within each of the pin holders is formed as a hole extending in a straight line through a center of the spherically rounded surface of the pin mounting structure between first and second ends of the pin mounting structure, wherein each of the pin holders additionally includes a first slot, perpendicular to the pin mounting surface, extending across the pin mounting structure and partially across the pin holder, displaced inward from the first end of the pin mounting structure, and a central part extending adjacent the first slot past a center of the spherically rounded outer surface of the holder, and wherein the at least one deformable portion of each of the pin holders includes a first deformable portion extending between the first slot and the first end of the pin mounting structure, a mounting hole formed within the housing, including a spherically rounded inner surface engaging the spherically rounded outer surface of the pin holder and an aperture extending outward through the housing between the spherically rounded outer surface and the inward-facing surface of the housing, a threaded inner surface, coaxial with the spherically rounded inner surface and the aperture about the central axis, wherein the central axis of each of the mounting holes is disposed at an angle different from an angle at which the central axis of each other mounting hole is disposed, so that the bone pins are held to converge within a region of convergence substantially shorter than the first distance and spaced apart from the elongated portion, and wherein each of the pin holders is rotationally adjustable within the elongated portion to vary a location of a pin within the region of convergence, a clamping member having a threaded outer surface and a rounded surface engaging the pin holder, wherein engagement between the threaded outer surface of the clamping member and the threaded inner surface of the mounting hole holds the pin holder in place between the rounded surface of the clamping member and the spherically rounded inner surface of the mounting hole, and additionally deflects the at least one deformable portion of the pin holder to hold the bone pin in place within the pin holder, wherein as each of the clamping members is rotated in a first rotational direction in contact with one of the pin holders, an engagement force between the spherically rounded surface of the pin holder and the internal mounting surface within the housing is increased to hold the pin holder in place within the housing, and deflection of the first deflectable portion of the pin holder is increased, moving a portion of the pin mounting hole within the first deflectable portion out of alignment with a portion of the pin mounting hole extending through the central part of the pin holder to hold the bone pin in place within the pin holder, and wherein as each of the clamping member is rotated opposite the first rotational direction in contact with one of the pin holders, the engagement force between the spherically rounded surface of the pin holder and the internal mounting surface within the housing is decreased to allow rotation of the spherically rounded surface of the pin holder within the internal surface of the housing and wherein the deflection of the first deflectable portion of the pin holder is decreased, returning the portion of the pin mounting hole within the first deflectable portion into alignment with the portion of the pin mounting hole extending through the central part of the pin holder to allow movement of the bone pin within the pin holder.

9. The apparatus of claim 8, wherein
each of the pin holders additionally includes a second slot, perpendicular to the pin mounting surface, extending across the pin mounting structure and partially across the pin holder, displaced inward from the second end of the pin mounting structure the central part of each pin holder extends between the first and second slots of the pin holder, the at least one deformable portion of each of the pin holders additionally includes a second deformable portion extending between the second slot and the second end of the pin mounting structure, as each of the clamping members is rotated in the first rotational direction in contact with one of the pin holders, deflection of the second deflectable portion of the pin holder is increased, moving a portion of the pin mounting hole within the second deflectable portion out of alignment with a portion of the pin mounting hole extending through the central part of the pin holder to hold the bone pin in place within the pin holder, and as each of the clamping members is rotated opposite the first rotational direction in contact with one of the pin holders, the deflection of the second deflectable portion of the pin holder is decreased, returning the portion of the pin mounting hole within the second deflectable portion into alignment with the portion of the pin mounting hole extending through the central part of the pin holder to allow movement of the bone pin within the pin holder.

10. The apparatus of claim 8, wherein
the elongated portion of the housing extends linearly in a first direction,
the elongated portion of the housing has a flat surface,
the pin mounting structures are disposed along a straight line within a first distance in the first direction along the elongated portion of the housing,
the area of convergence is significantly shorter in the first direction than the first distance, and
the central axis of each of the mounting holes extends toward the area of convergence, being disposed at an angle, relative to the flat surface, that is different from an angle, relative to the flat surface, at which the central axis of each other mounting hole is disposed.

11. The apparatus of claim 8, wherein
the elongated portion of the housing and the mounting holes forming portions of the at least three pin mounting structures extend along an arcuate line formed about an arc axis,
the area of convergence is formed around the arc axis, and
the central axis of each mounting hole is disposed perpendicular to the arcuate to extend to the arc axis.

12. The apparatus of claim 11, wherein
the housing additionally includes a linear portion extending from one end of the elongated portion parallel to the arc axis, and
the linear portion includes at least three additional pin mounting structures, spaced apart along a straight line parallel to the arc axis holding bone pins extending toward the arc axis.

13. The apparatus of claim 11, wherein
the housing additionally includes a linear portion extending from each end of the elongated portion in a first direction, parallel to the arc axis, and
each linear portion includes at least three additional pin mounting structures, spaced apart along a straight line parallel to the arc axis holding bone pins extending toward the arc axis.

* * * * *